United States Patent [19]
Mor

[11] Patent Number: 6,088,020
[45] Date of Patent: Jul. 11, 2000

[54] HAPTIC DEVICE

[75] Inventor: Andrew B. Mor, Pittsburgh, Pa.

[73] Assignee: Mitsubishi Electric Information Technology Center America, Inc. (ITA), Cambridge, Mass.

[21] Appl. No.: 09/133,827

[22] Filed: Aug. 12, 1998

[51] Int. Cl.[7] .................................................. G09G 5/00
[52] U.S. Cl. .................... 345/156; 434/262; 318/628; 345/184
[58] Field of Search ................... 345/156, 157, 345/161, 184, 433, 420; 364/578; 318/561, 628; 434/262, 274

[56] References Cited

U.S. PATENT DOCUMENTS

| | | | |
|---|---|---|---|
| 5,625,576 | 4/1997 | Massie et al. | 364/578 |
| 5,694,013 | 12/1997 | Stewart et al. | 318/561 |
| 5,704,791 | 1/1998 | Gillio | 434/262 |
| 5,767,839 | 6/1998 | Rosenberg | 345/161 |

*Primary Examiner*—Richard A. Hjerpe
*Assistant Examiner*—Francis Nguyen
*Attorney, Agent, or Firm*—Dirk Brinkman

[57] ABSTRACT

Apparatus is provided to extend the number of active degrees of freedom of a haptic interface to provide the user with the feel of a tool which is cantilevered over obstacles or which experiences frictional drag along its shaft. This is accomplished by providing two additional active degrees of freedom while not limiting the rotation or translation of the handle that the user is grasping. The apparatus constrains, through a 4 degree of freedom gimbal, the shaft of the tool handle, whose tip is controlled by another 3 spatial degree of freedom haptic device. The shaft of the tool slides and rotates in a sleeve bearing or collar which is mounted in a 2 degree of freedom gimbal. The gimbal is rigidly connected to a 2 degree of freedom parallel planar manipulator, with both degrees of freedom of the planar manipulator being powered by actuators used to generate the requisite haptic forces. The use of this device provides users with a 5 degree of freedom device, through which they can feel forces and moments, instead of only point forces which are generated by 3 degree of freedom devices. This is useful when performing simulations where a portion of the tool removed from the tip may contact an obstruction instead of just the tip.

7 Claims, 11 Drawing Sheets

HAPTIC DEVICE

FIELD OF THE INVENTION

This invention relates generally to the field of human/computer interaction and more specifically to haptic interfaces.

BACKGROUND OF THE INVENTION

Virtual Reality (VR) technology has spread to many different applications in the past few years. This spread has been accelerated through the availability of devices that easily allow interaction with virtual interaction with virtual environments. These new devices range from stereo visual displays and passive tracking devices, to more active mechanisms that involve force feedback. These force feedback devices, which interact with the users sense of touch, their haptic sense, allow for greater realism and performance when completing tasks. Being able to feel contact between two objects produces much stronger cues to the user than can be produced with visual feedback. Haptic interfaces display forces to the users hand through the use of motors or actuators, thereby mimicking the feel of physical objects. These devices, in conjunction with conventional visual displays, allow the creation of many different types of simulators, from a typical block in hole problem to surgical simulations. The devices can also be used for entertainment in video games and scientific exploration by examining haptic models of remote environments, which could range from atomic scale molecular models to planetary scale virtual maps. Haptic interfaces can also be used as general masters in teleoperation systems, where the user controls a machine at a remote site through sensations generated by the interface based on what the remote machine experiences.

In general, haptic interface systems consist of an apparatus which will physically sense the position of and apply forces to the user, and computational hardware to determine the users position, perform simulation tasks, and determine the forces to feed back to the user so that he/she can feel the result of moving the on-screen object into contact with and sometimes into another on-screen object.

The computational hardware can also contain the simulation of the visual display, so as to maintain synchronism between the haptics and the graphics subsystems.

There are a handful of different haptic mechanisms commercially available which vary greatly in design. These different mechanisms range greatly from simple 2 degree of freedom (DOF) computer mouse type designs to a 7 DOF, cable driven mechanism. Both devices utilize low friction, low inertia mechanisms. Other devices are built around standard robot mechanisms, with sensors to detect movement so that they can perform inertia compensation, to reduce the perceived mass of the device. Some mechanisms include force sensors in the tool handle to sense the forces felt by the user, while others forego such sensors to simplify the design and reduce cost.

3 DOF devices provide the most generality in workspace without limiting the user to a planar surface, but are limited to providing only position feedback, usually of the tip of a device or tool, which inadequate for many simulations. This is because the shank of the tool may contact an obstacle or another portion of the body it is inserted into which causes a torque to be applied to the tool. Prior 3 DOF devices have no way of simulating this torque, so the user cannot feel its effect. Devices like the aforementioned 7 DOF haptic interface are very complex, and have limited mechanical stiffness.

By way of background, minimally invasive surgical simulation, where tools are inserted into the body through small incisions and the procedure is observed on a video monitor, often require more than 3 DOF so that an individual can feel all of the effects on the tools as it is inserted into the body. This includes, for instance, the cantilevering of the shank of a probe on a tendon as the point of the scalpel proceeds in towards its intended position.

There is therefore a need for a device which can simulate the forces felt by both the tip and the shaft of a medical instrument inserted within the body.

More particularly, in the field of surgical simulation, there is a need to provide a trainee with the feel of the instrument as he or she uses the instrument in a simulated environment. Here a training scenario may involve manipulating a simulated scalpel on-screen, at which, for instance, a patients knee is presented. Through so-called voxel representation of the knee, various parts of the knee can be given densities and penetration characteristics resembling a real knee.

In the past, such virtual reality representations have been used to permit the generation of forces on the tip of the instrument used to drive the virtual reality instrument so as to give the trainee feeling of actually penetrating the given part of anatomy. However, the 3D haptic devices, called Phantoms, cannot give the trainee the sensation of what is happening when not only does the probe tip touch a given part of the anatomy, but also when the tool shaft touches part of the anatomy as the tool is manipulated.

In short, what is missing is a way to impart the sensation of the tool cantilevered on some structure or obstacle which is removed from the tip of the tool, as would the case of the tool passing over a ligament on its way to where the tip of the probe is present.

SUMMARY OF THE INVENTION

In order to provide sensation for forces not only on the tip of a tool, but also along the shaft of the tool, an apparatus is provided to generate pitch and yaw forces to the shaft of the tool which simulate the counter forces encountered when the tool shaft touches an object removed from its tip. In one embodiment, this is accomplished by using a collar slipped over the tool shaft in which the tool can easily translate and rotate, i.e., a gimbaled sleeve.

Pitch and yaw forces are applied by actuators to the collar to move the collar in orthogonal directions in a plane at an angle to the longitudinal centerline of the tool.

The actuators are driven in such a manner that the sum of the forces applied to the tip of the tool and those applied by the collar give a realistic feel on the handle of the tool to simulate not only what is happening at the tip of the tool, but also what is happening along its shank as the tool passes over structures during inward movement or penetration into an on-screen graphical object.

Thus, the subject invention is one that provides additional degrees of force feedback to a 3 degree of freedom haptic device involving all spatial, not rotational, degrees of freedom. This invention is particularly useful for the simulation of minimally invasive surgical techniques, where a surgical instrument is inserted through a small portal into the body.

The apparatus consists of a grounded planar mechanism through which the shaft of a surgical instrument passes through. By grounding most of the apparatus's mass, inertia and frictional forces are reduced, thereby increasing the sense of realism to the user when compared with a conventional serial device, where masses such as the motors are not grounded. The mechanism is a classical five-bar mechanism, which has two powered degrees of freedom, with a 4 DOF gimbal on the end. The gimbal consists of a 2 DOF universal joint, with a linear/rotational sleeve bearing in the outer link of the universal joint providing the additional 2 degrees of freedom. The shaft of the tool the user grasps passes through the linear/rotational sleeve, and connects to a gimbal containing 3 free degrees of freedom, which itself connects to a 3 DOF haptic device that drives the tip of the tool.

The subject invention is thus directed towards a system for providing an interface between a human and a computer which mimics the physical embodiment of minimally invasive surgery, and other similar situations. The subject invention may be viewed as constraining the passage of the shaft of the tool's handle to be within a certain planar area, which is the tool's workspace. An analogy would be to view the local volume that the user is interacting with to be within an imaginary cube. The external 3 DOF interface controls the position of the tip of the tool within the cube, while the shaft of the tool must pass through the center of the front face of the cube, so that the point that the shaft of the tool must pass through is controlled by the subject apparatus.

In summary, apparatus is provided to extend the number of active degrees of freedom of a haptic interface to provide the user with the feel of a tool which is cantilevered over obstacles or which experiences frictional drag along its shaft. This is accomplished by providing two additional active degrees of freedom while not limiting the rotation or translation of the handle that the user is grasping. The apparatus constrains, through a 4 degree of freedom gimbal, the shaft of the tool handle, whose tip is controlled by another 3 spatial degree of freedom haptic device. The shaft of the tool slides and rotates in a sleeve bearing or collar which is mounted in a 2 degree of freedom gimbal. The gimbal is rigidly connected to a 2 degree of freedom parallel planar manipulator, with both degrees of freedom of the planar manipulator being powered by actuators used to generate the requisite haptic forces. The use of this device provides users with a 5 degree of freedom device, through which they can feel forces and moments, instead of only point forces which are generated by 3 degree of freedom devices. This is useful when performing simulations where a portion of the tool removed from the tip may contact an obstruction instead of just the tip.

BRIEF DESCRIPTION OF THE DRAWINGS

These and other features of the Subject Invention will be understood in conjunction with the Detailed Description taken in conjunction with the Drawings of which.

DETAILED DESCRIPTION OF THE PREFERRED EMBODIMENT

Figure 1:
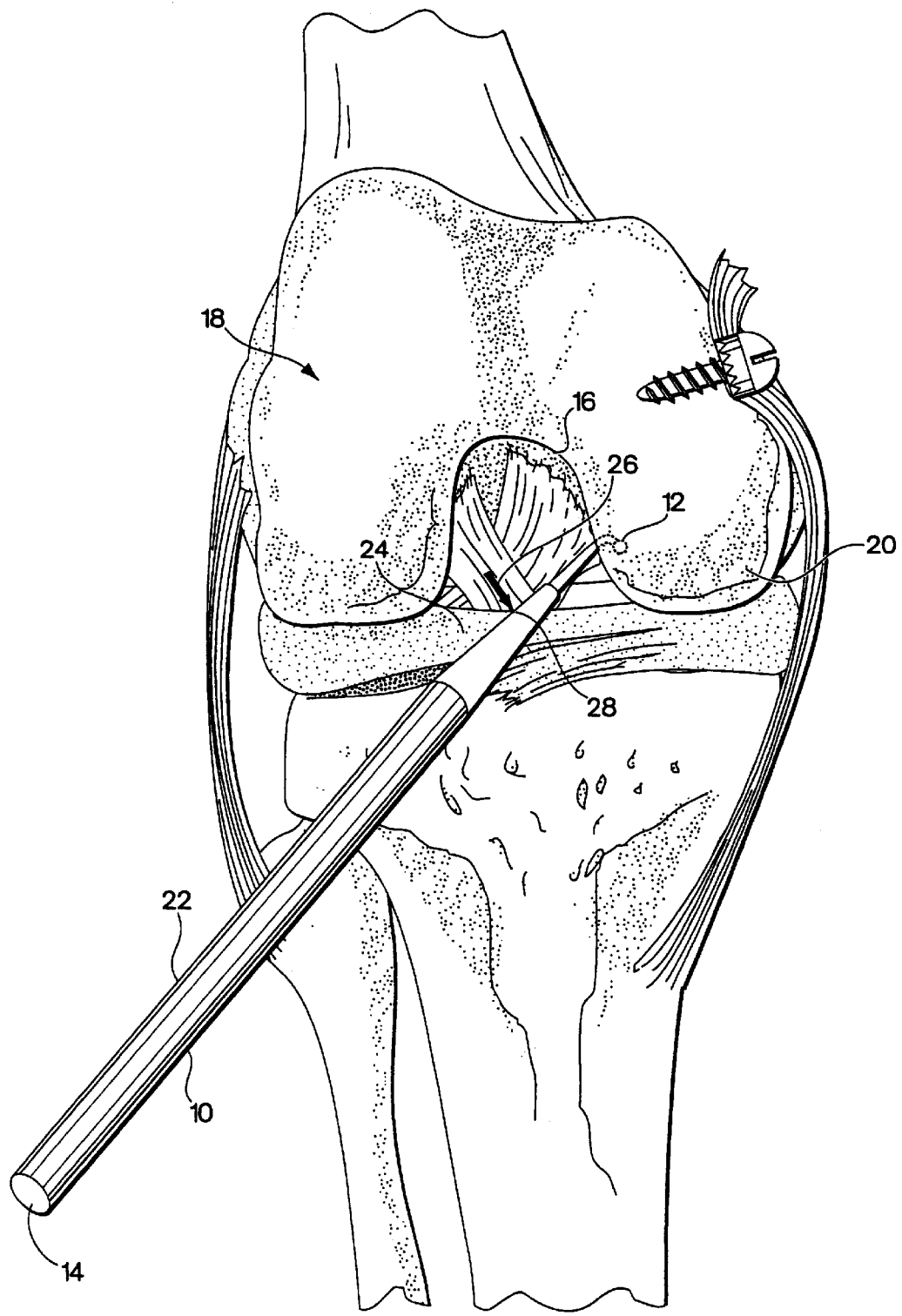
FIG. 1 is a diagrammatic representation of a knee in which a probe is inserted into the notch of the femur, indicating the cantilevering of the probe on the meniscus of the knee, indicating the generation of forces not only on the tip of the probe, but also at a point intermediate between the tip and the end thereof.

Referring now to FIG. 1, in a typical simulated knee operation, a probe or tool 10 having a tip 12 and a distal end 14 is pushed into an area designating by notch 16 of femur 18 in which the probe is utilized to sense the condition of the cartilage of the medial condial 20. In actuality, during operation there will be a counter force generated back along the shaft 22 of tool 10 when the tip of the probe 12 contacts tissue.

Typically, in a haptic environment, for training or other purposes, a virtual knee is provided to the trainee and tool 10 is driven by a so-called haptic device which provides counter forces on the tool when an on-screen version of tip 12 comes into contact with an on-screen version of tissue. One such haptic device is known as the Phantom and is available from Sensable Technologies, Inc. of Cambridge, Mass.

The problem with a 3D actuating device such as the Phantom is that there is no ability to simulate the passage of a portion of the tool over an area such as a meniscus 24 which exerts a force 26 on a point 28 of the tool which is intermediate the tip and its end. This, in essence, in the actual world provides a cantilevering force which indicates to the individual that not only has the tip of the tool proceeded into a dense tissue area, but also that its shank has encountered an obstacle during the probing process.

Figures 2A, 2B:
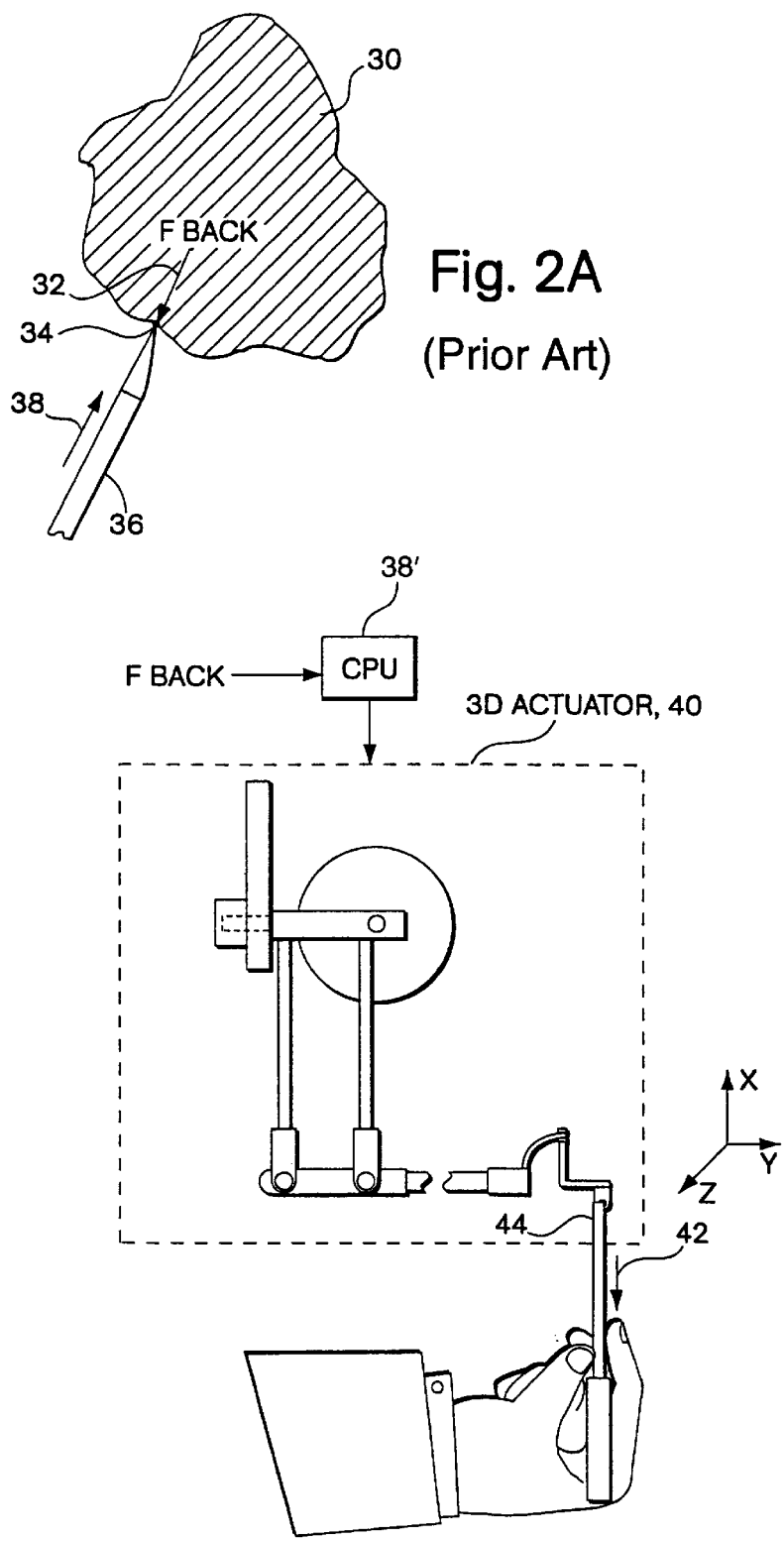
FIG. 2A is a diagrammatic representation of an object producing a force on the tip of the probe of FIG. 1 in a backward direction as the probe is inserted into the object.
FIG. 2B is a diagrammatic representation of apparatus including a 3D actuator for simulating the tip force on a probe through the utilization of a 3D haptic device, in which the backwards force represented in FIG. 2A is presented to the individual at the tool handle.

Referring to FIG. 2A, in the prior art, an object 30 produces a backward or counter force 32 on the tip 34 on a tool 36 which is moved in the direction of arrow 38 to probe the object.

In order to give the individual the sense of what is happening in the haptic environment, the counter force is provided to a CPU 38' which drives a 3D actuator 40 of the type described above to produce a counter force 42 on a tool 44, with the 3D actuator being able to provide components of this force in 3 directions. As a result, these types of actuators are called 3 degree of freedom devices. From the foregoing discussion, it will be apparent that such devices are incapable of providing a feel to the tool which incorporates the tool running over a simulated obstacle.

Figure 3:
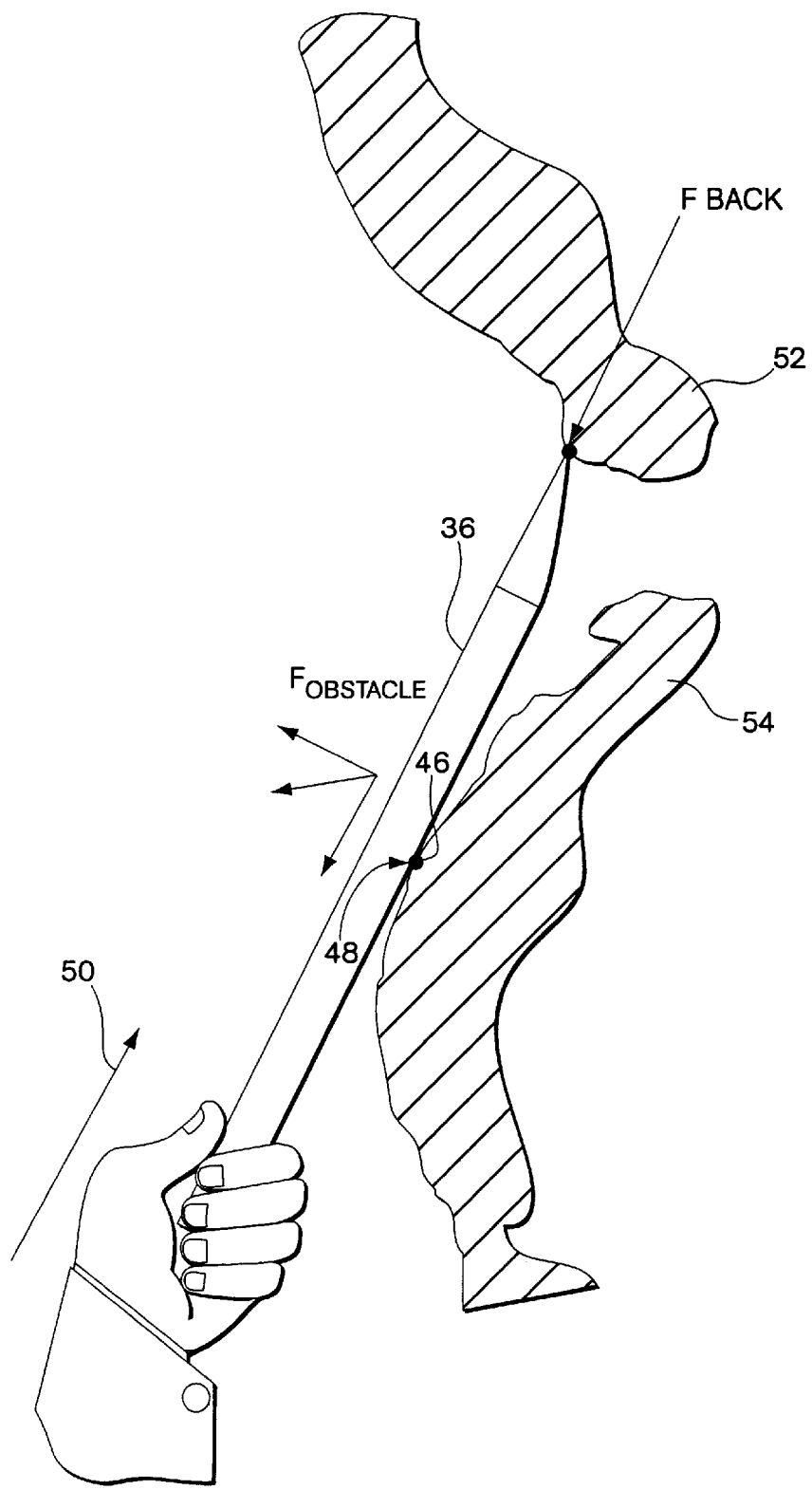
FIG. 3 is a diagrammatic representation of the forces on a rigid tool which are generated not only at tip of the tool, but at a point intermediate the tip and the end of the tool in which in the illustrated embodiment, the tool passes over an obstacle which is in frictional contact with the rigid tool surface.

This situation is illustrated in FIG. 3 in which tool 36 has a point 46 on its shaft encountering an obstacle 48 which provides a counter force along the length of the tool as the tool is thrust in the direction of arrow 50 into the object, here pictured at 52. It will be appreciated that the forces act on the surface of the tool by friction and by displacement of the tool in a direction normal to the direction of travel of the tool as it is used as a probe or cutting device. Of course, these counter forces are provided by the contacting of a portion of the tool with object 54.

Figure 4:
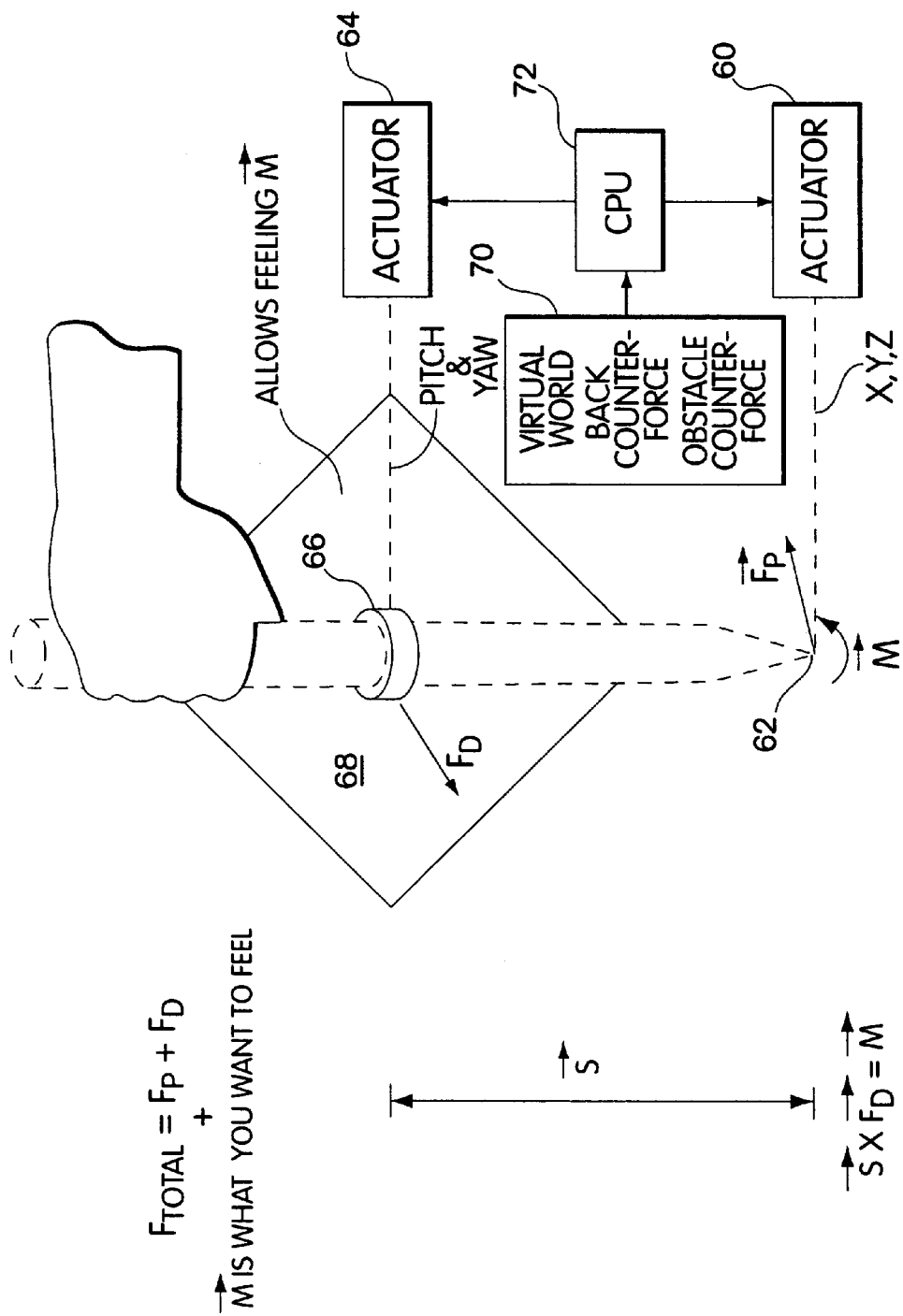
FIG. 4 is a diagrammatic representation of the subject system in which forces applied intermediate the tip and the of a rigid tool are applied in the haptic manner to simulate the feel to the tool as the tool transits over the obstacle shown in FIG. 3, with the forces applied intermediate the tip and the of the tool being added to the forces applied to the tip of the tool to allow the haptic device to simulate situations in which forces are applied not only to the tip of the tool, but also to the shank thereof.

Referring now to FIG. 4, a way in which the forces on tool are made of approximate not only the tools tip contacting an object, but also the tool contacting an obstacle, in one embodiment, includes not only an actuator 60 which controls 3-dimensional forces on the tip 62 of the tool, but also an actuator 64 which is mechanically linked to a sleeve or collar 66 through which the tool passes and is gimbaled. As will be seen, the actuator 64 controls the pitch and yaw forces applied to the sleeve or collar and thus to the tool. Note, these forces are applied in a plane 68.

The force applied to sleeve or collar 66 is labeled as $\vec{F}_D$ whereas the forces applied to the tip are labeled $\vec{F}_P$. The force that the individual should feel is $\vec{F}_T$, which is the sum of the forces $\vec{F}_P$ and $\vec{F}_D$. The utilization of actuator 64 to provide forces in the pitch and yaw directions allows the individual to feel the effects of a force that is applied intermediate the tip and the end of the tool, noting of course, that this force is applied a distance $|\vec{S}|$ from the tip.

It will be appreciated that if one applies yaw and pitch forces at a point intermediate in the length of the tool one generates a moment, here labeled $\vec{M}$, in which $\vec{M}$ is defined to be the cross product of the vector $\vec{S}$ and the vector $\vec{F}_D$. It is this moment which is felt by the individual when he/she grasps or otherwise contacts the tool handle and which gives the individual the sensation of not only the tip forces, but also the intermediate forces on the tool as the tool is manipulated in a virtual space.

In order to generate such forces, for a model of an object in a virtual world, the model characterizes the counter force generated as the tool is pushed into the object as well as the obstacle counter force which would be modeled after real life situation, in which the tools are passed over an obstacle, the aforementioned meniscus. The virtual world counter forces are established as will be described as illustrated at 70 and provided to a CPU 72 which drives actuators 60 and 64 so as to provide a haptic feedback to the individual in accordance with the parameters of the virtual world procedure.

Figure 5:
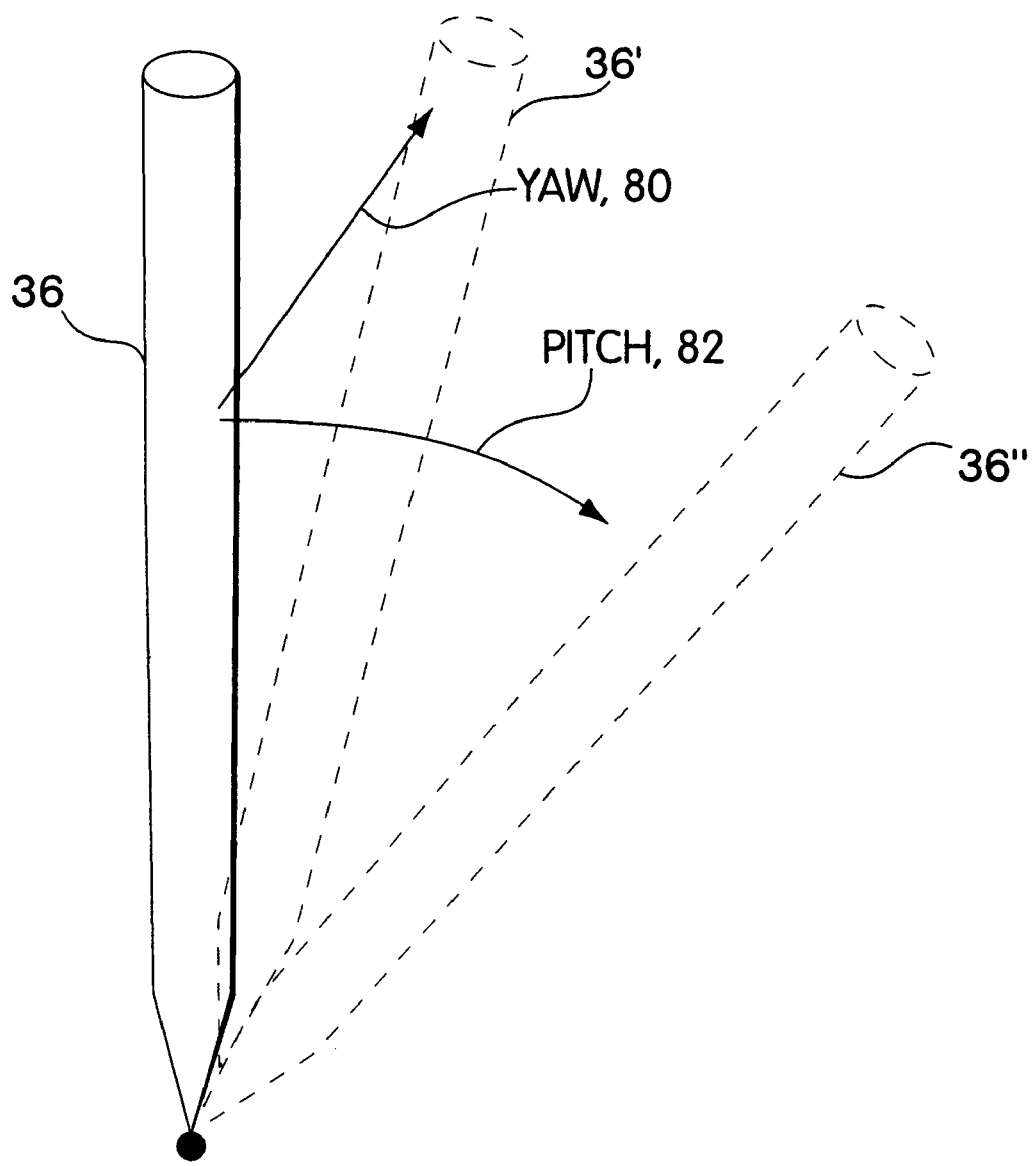
FIG. 5 is diagrammatic representation of a 5 degree of freedom haptic device of the subject invention in which 3 degrees of freedom relate to the point of the tool, whereas the pitch and yaw forces making up the last 2 degrees of freedom are applied intermediate the tip and the end of the tool to cause the tool to move in the pitch and yaw directions as illustrated.

Referring now to FIG. 5, the subject device thus provides a 5 degree of freedom haptic feedback device in which not only are forces on the point of the instrument accounted for, but also forces applied intermediate the point and the of the rigid tool. These forces are illustrated at 80 and 82 to depict the movements of tool 36, with the individual feeling the yaw and pitch motions generated by the subject system as illustrated in dotted outline 36' and 36".

To summarize, the subject device provides force feedback motions to the tool, which are generated both at the tip and at some point intermediate the tip and the end of the tool to provide the tool wit motions in the X, Y, Z position of the tip, with yaw and pitch motions referenced to the tip.

Figure 6:
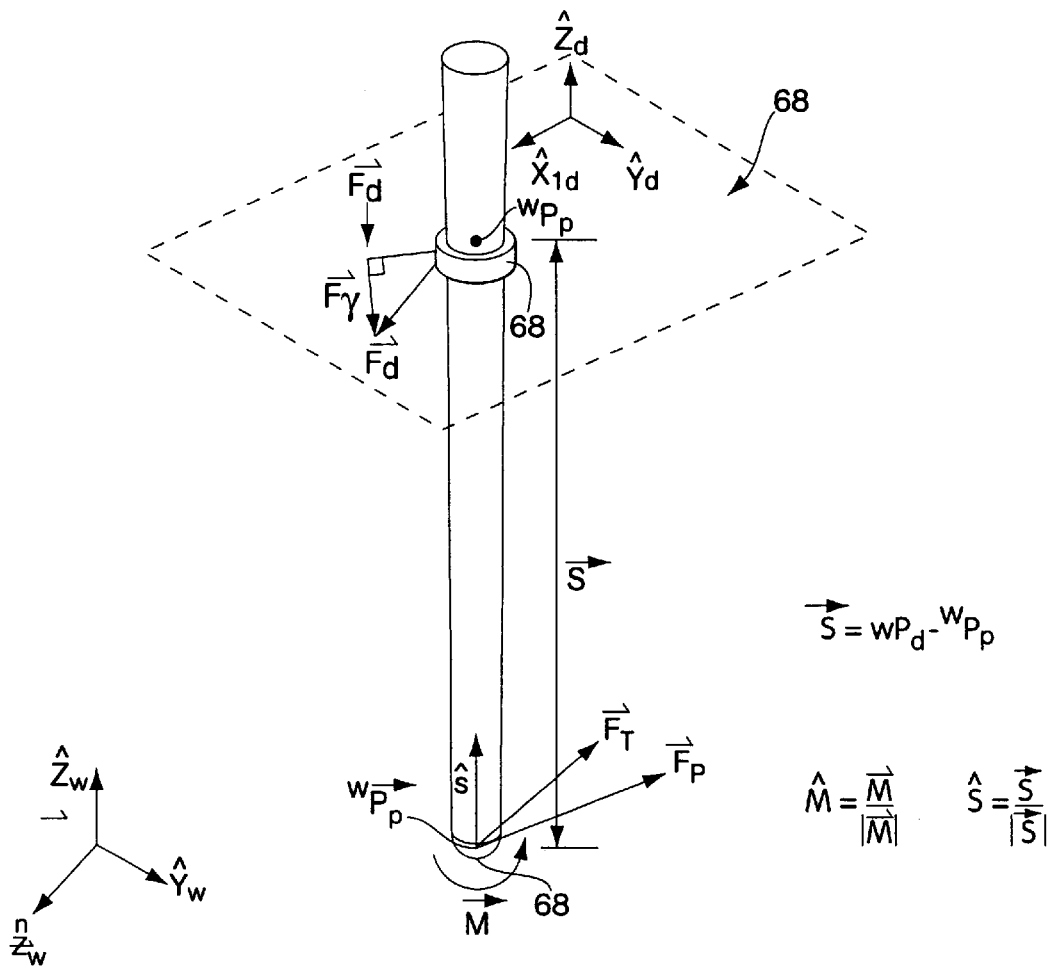
FIG. 6 is a diagrammatic representation of the subject system in which forces are applied to not only to the tip of the tool, but also t a point intermediate the tip and the end of the tool in which the mathematical relationships of the forces applied at the aforementioned points are determined.

Referring now to FIG. 6, the way in which the forces at the tip and the point intermediate the tip and the end are generated as illustrated by the following relations.

Figure 8:
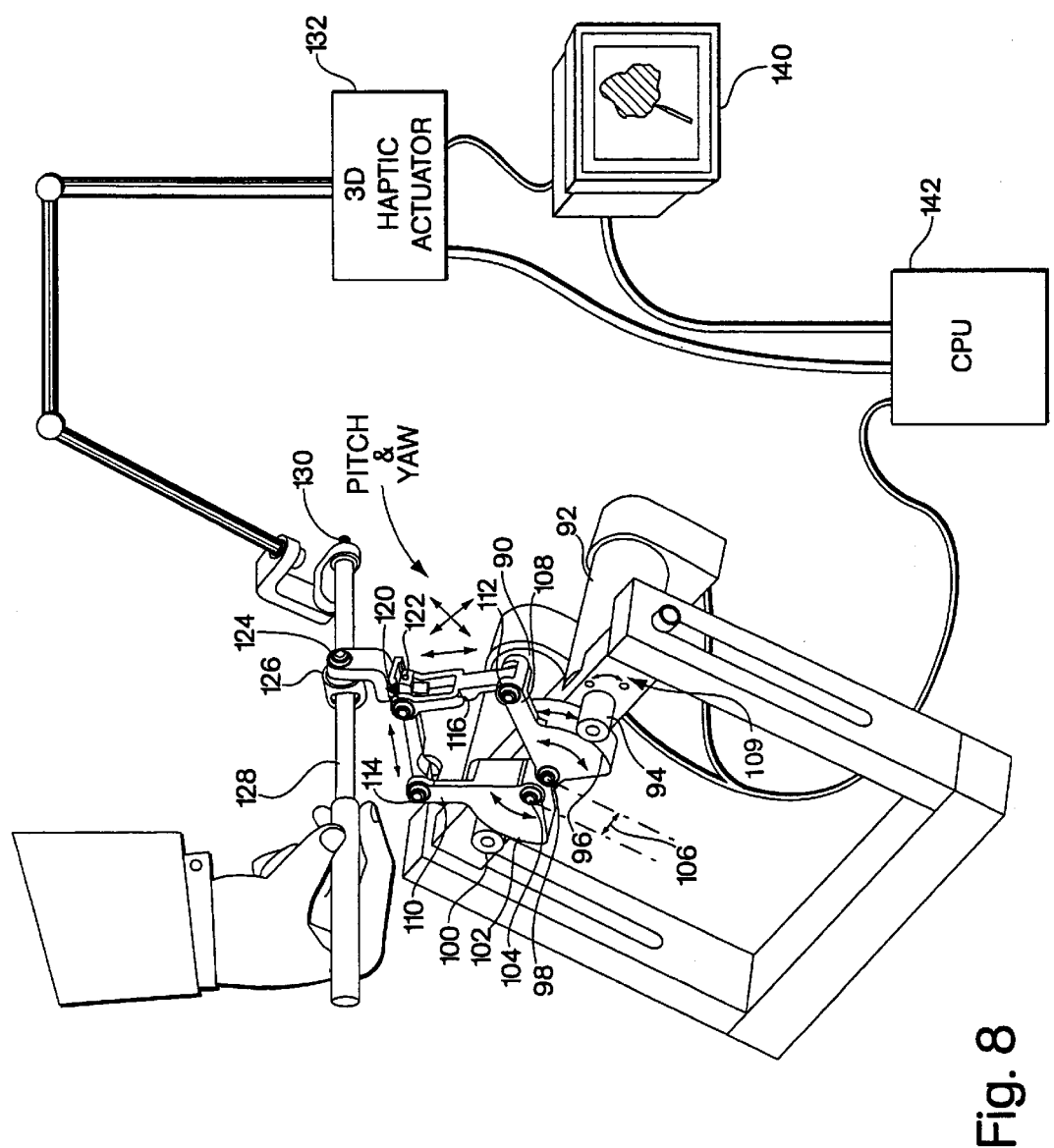
FIG. 8 is a perspective view of the ground apparatus used to generate the pitch and yaw forces which are applied to a point intermediate the tool involving a five bar mechanism drive for the sleeve or collar of FIG. 7 in which two of the arms of the five bar mechanism are driven by rotary actuators against a cam service which serves to move the two arms in the directions shown, thus to provide a pitch and yaw motion to the central pivot point of the device attached to the gimbaled sleeve or collar through which the tool is inserted.

Given the values of $\vec{M}$ and $\vec{F}_T$ that should be felt by the user, and the vector $\vec{S}$ between the tip position of the tool and the linear bearing of a five bar mechanism shown in FIG. 8, the forces to generate at the tip and through the collar can be determined. Let w represent the world coordinate frame where all positions and forces are measured and d be the coordinate frame of the five bar mechanism where $\hat{Z}_d$ is normal to the plane that the device moves in. Then, $$\overset{w\rightarrow}{P}_p$$

is the position of the tip of the tool and $$\overset{w\rightarrow}{P}_d$$

is the position of the five bar mechanism. $\vec{S}$ is the vector from the five bar mechanism position to the position of the tip of the tool, while $\hat{S}$ is the normalized direction of $\vec{S}$. Similarly, $\hat{M}$ is the normalized direction of $\vec{M}$.

First, the force, $\vec{F}'_d$, is calculated at the five bar mechanism position which would generate the moment $\vec{M}$:

$$\vec{F}_d = (\hat{M} \times \hat{S}) \frac{|\vec{M}|}{|\vec{S}|}$$

$\vec{F}'_d$ will normally not lie in the plane define by the five bar mechanism, and will satisfy the moment equation, $\vec{M} = \vec{S} \times \vec{F}'_d$. It is also always perpendicular to the vector $\vec{S}$.

Next, the force $\vec{F}'_d$ is projected onto the plane of the five bar mechanism, so that the force applied by the device, $\vec{F}_d$, will also satisfy the equation $\vec{M} = \vec{S} \times \vec{F}_d$. This projection force, which is perpendicular to the force, $\vec{F}'_d$, is generated by:

$$\vec{F}_y = \left( -\frac{\hat{z}_d \cdot \vec{F}'_d}{\hat{z}_d \cdot \hat{S}} |\vec{F}_d| \right) \hat{S}$$

The force that will be generated by the five bar mechanism is the vector sum of $\vec{F}'_d$ and $\vec{F}_y$:

$$\vec{F}_d = \vec{F}'_d + \vec{F}_y$$

The force applied to the tip of the tool is $\vec{F}_p = \vec{F}_T - \vec{F}_d$, to maintain the total force being applied to the user.

It should also be noted, that if the five bar interface is replaced with a general 3 DOF device, the equation for $\vec{F}'_d$ above would be used for the calculation of $\vec{F}_d$, since the device will be able to apply any force, not just forces in a plane. The force applied to the tip of the tool would remain $\vec{F}_p = \vec{F}_T - \vec{F}_d$.

Figure 7:
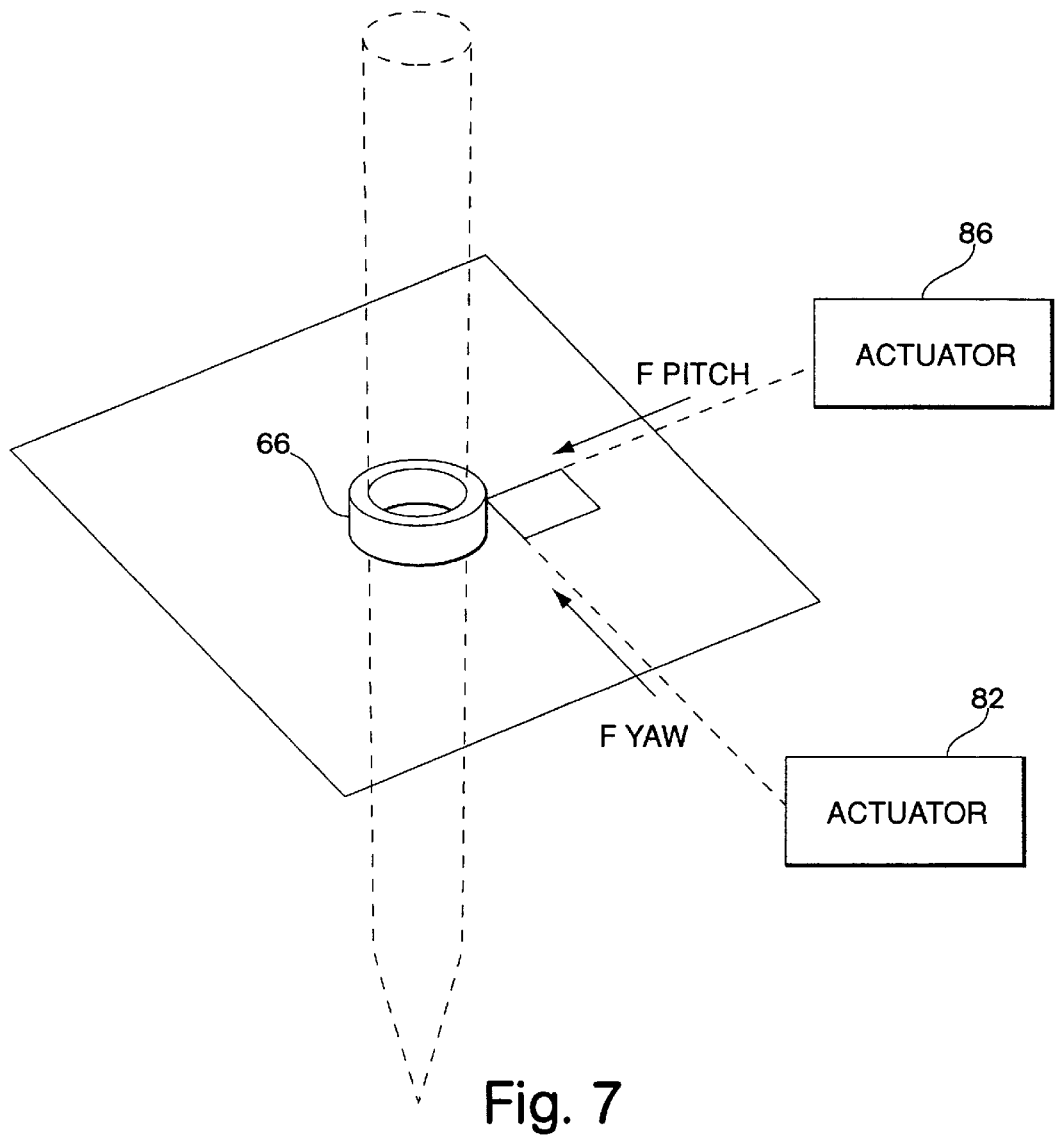
FIG. 7 is a diagrammatic representation of the utilization of pitch and yaw actuators to provide forces on a sleeve or collar through which the tool slips and is gimbaled, thereby to provide a feel to the tool which incorporates not only tip forces, but also forces applied intermediate the tip and the end of the tool.

As illustrated in FIG. 7, what is now described is an actuator to provide the aforementioned pitch and yaw forces which are applied to sleeve or collar 66 in one embodiment by two actuators 84 and 86 which correspond to the actuation depicted by actuator 64 in FIG. 4. In one embodiment, this is accomplished through a pentagram linkage system, referred to as a five bar linkage.

As illustrated in FIG. 8, the actuators include motors 90 and 92, each of which have capstans 94 which are in contact with a sector 96 pivoted about a pivot point 98. Motor 90 drives capstan 100 which communicates with sector 102 to drive the sector about pivot point 104. It is noted that these two pivot points are separated by a distance 106 in a plane defined by frame 109 which carries the motors, the sectors and pivot points in a grounded configuration. In the embodiment shown, the frame constitutes a mounting bar for the apparatus.

It will be seen that sectors 96 and 102 have extensions 108 and 110 respectively, which through pivots 112 and 114 at their distal ends drive arms 116 and 118 joined at their distal ends at pivot 120. An extension to arm 118, here illustrated at 122, is coupled to a gimbaling device 124 which carries sleeve or collar 126 through which tool 128 passes.

The tip 130 of tool 128 is driven by 3D haptic actuator 132 in a standard fashion such that 3D actuator 132 provides the 3 DOF haptic actuation for the tip of the tool, whereas sleeve or collar 126 and the five bar linkage drives sleeve or collar 126 to provide the requisite forces along the length of the tool to simulate forces applied to the tool in accordance with the virtual modeling.

In one haptic feedback scenario, a monitor 140 provides a visual indication of the tool and an object probed by the tool, with a CPU 142 controlling motors 90 and 92.

Figure 9:
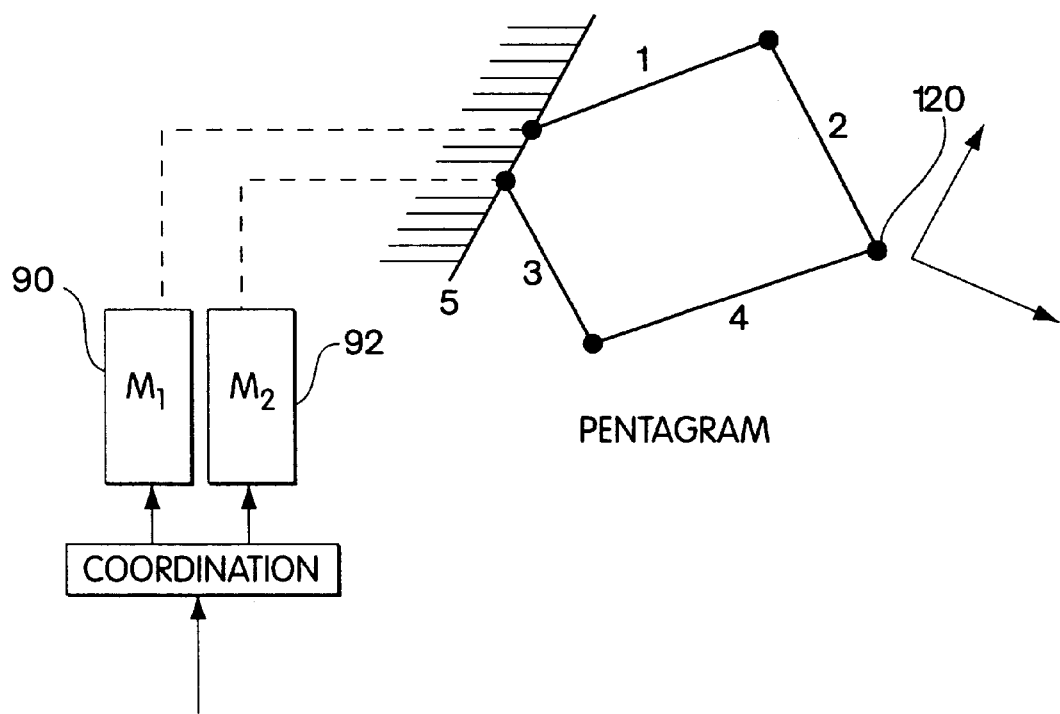
FIG. 9 is a block diagram illustrating the coordination of the motor drives to drive the aforementioned arms in FIG. 8 to achieve movement of the pentagram and thus the yaw and pitch motions, and, FIG. 10 is a detailed plan view of the pentagram yaw pitch actuator of FIG. 8 illustrating the critical dimensions used to determine the position of the endpoint of the pentagram.

Referring to FIG. 9, how motors 90 and 92 are driven and coordinated to provide the appropriate pitch and yaw movements of pivot 120 is now described.

Figure 10:
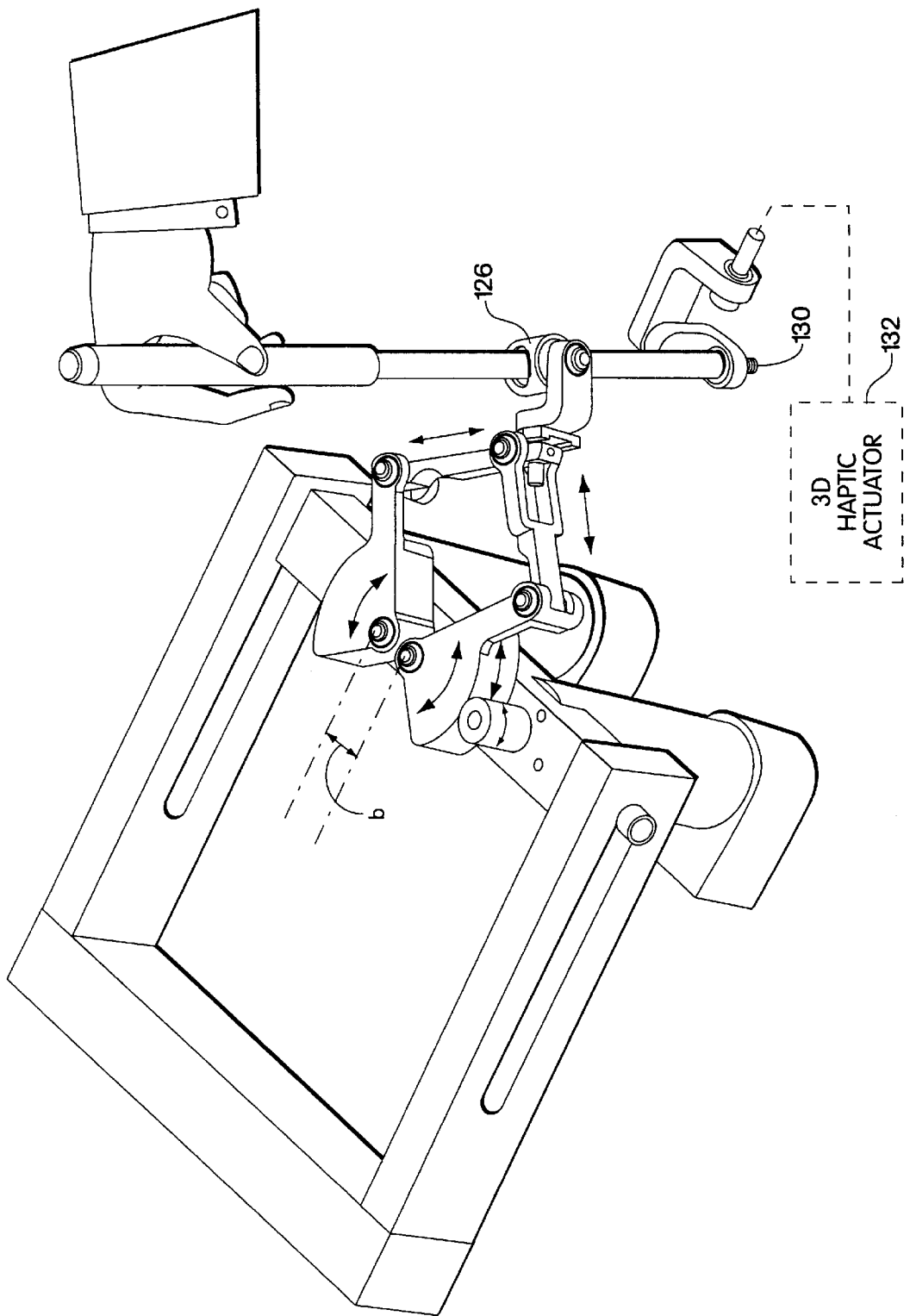

Referring now to FIG. 10, b is the horizontal distance between the proximal end of each of the two inner links and the origin of the workspace O. $l_i$ is the length of the ith link. $\theta_i$ is the angle of the ith link. $\theta_{d3}$ and $\theta_{d4}$ are two of the interior angles of the triangle formed by the two outer links and the line joining the distal ends of the inner links. a is the vertical distance and d is the horizontal distance between the distal ends of the inner links, while c is the shortest distance between them and $\theta_a$ is the angle between c and the horizontal, and has a negative value in FIG. 10.

Then d, a, and c are determined through simple geometry, and $\theta_a$ is the inverse tangent of a over c. $\theta_{d3}$ and $\theta_{d4}$ are calculated using the law of cosines, and then $\theta_3$ and $\theta_4$ are once again determined through simple geometry. The position of the endpoint of the five bar mechanism, (x,y), is then determined through geometry, where $l_5$ is the distance between the distal end of the outer links and the center of the gimbal along the axis of link 4, here notes as 140. $l_6$ is the distance between the distal end of the outer links and the center of the gimbal normal to the axis of link 4. The Jacobian J is calculated in the usual manner to facilitate the determination of the motor toques, $\tau$ to apply to the actuators to achieve the desired force $\vec{F}_d$. The equations described above are as follows:

$$d = 2b + l_1 \cos\theta_1 - l_2 \cos\theta_2$$

$$a = l_1 \sin\theta_1 - l_2 \sin\theta_2$$

$$c = \sqrt{a^2 + d^2}$$

$$\theta_a = a\tan\frac{a}{d}$$

$$\theta_{d3} = a\cos l_3^2 + c^2 - \frac{l_4^2}{2l_3 c}$$

$$\theta_{d4} = a\cos l_4^2 + c^2 - \frac{l_3^2}{2l_4 c}$$

$$\theta_3 = \pi - \theta_{d3} + \theta_a$$

$$\theta_4 = \theta_{d4} + \theta_a$$

$$x = b + l_1 \cos\theta_1 + l_3 \cos\theta_3 + l_5 \cos\theta_4 + l_6 \cos\left(\theta_4 + \frac{\pi}{2}\right)$$

$$y = l_1 \sin\theta_1 + l_3 \sin\theta_3 + l_5 \sin\theta_4 + l_6 \sin\left(\theta_4 + \frac{\pi}{2}\right)$$

$$J = \begin{bmatrix} \frac{\partial x}{\partial \theta_1} & \frac{\partial x}{\partial x_2} \\ \frac{\partial y}{\partial \theta_1} & \frac{\partial y}{\partial \theta_2} \end{bmatrix}$$

$$\tau = J^T \vec{F}_d$$

Figure 11:
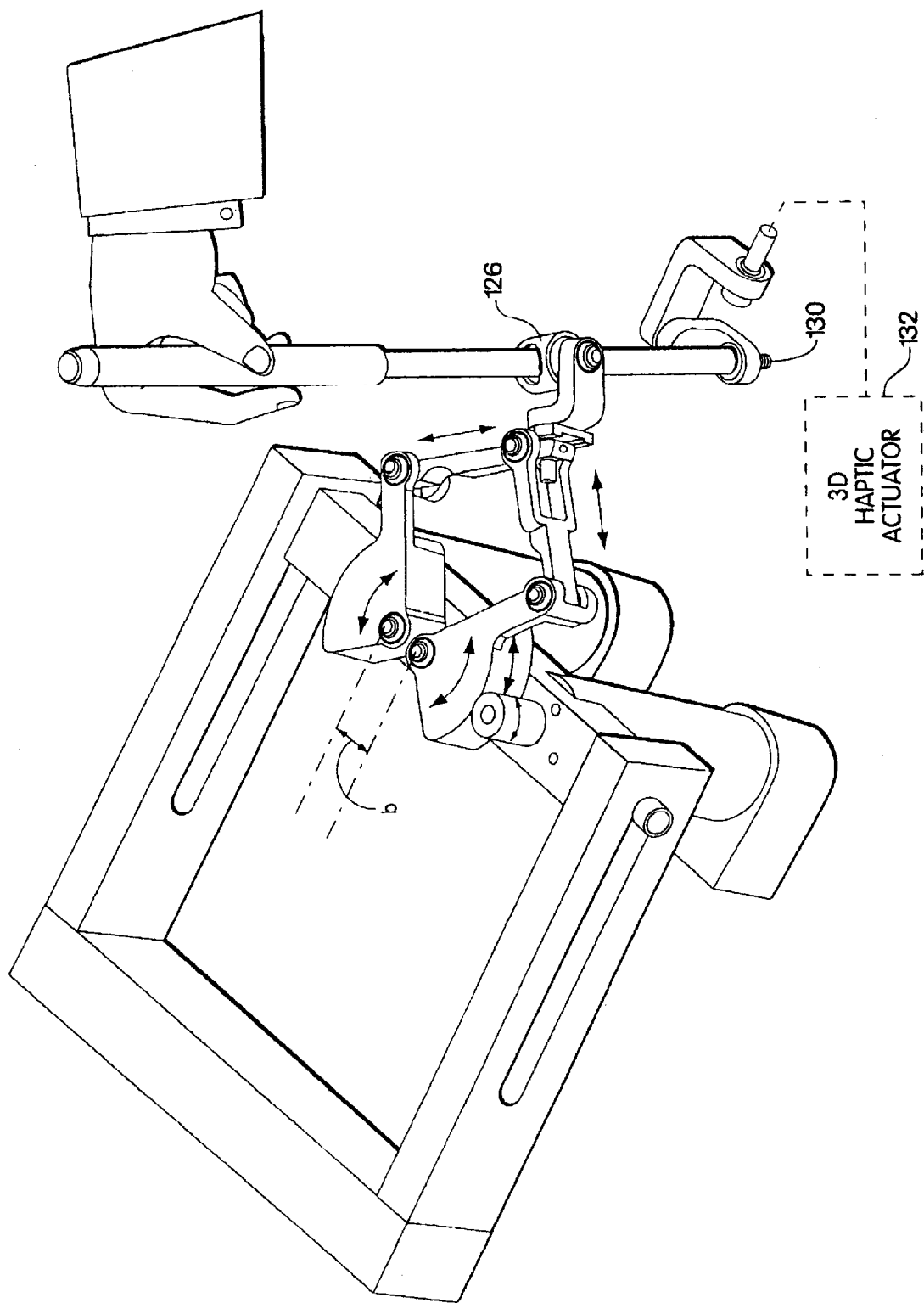
FIG. 11 is a detailed perspective view of the pentagram yaw pitch actuator of FIG. 8 illustrating the relationship between the distance between the pivot points of the first two pentagram arms and the motion of sleeve or collar through which the tool passes.

In summary and referring now to FIG. 11, what is provided is a haptic force feedback device which includes a 3D haptic actuator to drive the tip 130 of the tool, whereas a unique five bar linkage system coupled to gimbaled sleeve or collar 126 provides haptic feedback for forces generated in the modeling scenario intermediate the tip and the end of the tool. The combination of the forces applied at the tip and by the sleeve or collar provide the individual with the realistic force feedback representation of what would be happening to a tool which is utilized to probe an object, but which passes over some sort of an obstacle which also provides forces on the tool itself.

A pseudocode program for implementation of one embodiment of the subject invention is now presented, where loop ( ) is called repeatedly to perform the simulation:

```
Loop()
{
three_vector phantom_pos;
three_vector dev_pos;
three_vector total_force;
three_vector total_moment;
three_vector phantom_force;
three_vector dev_force;
/*
 * transformation matrix is the matrix to convert the devices position in its
 * local coordinate from into the world coordinate frame
 *
 * dev_normal is the normal to the plane of the device, measured in the
 * world frame
 */
matrix    transformation_matrix;
three_vector   dev_normal
phantom_pos = get_phantom_pos ();
dev_pos = get_device_pos ();
{
/*
 * perform simulation here
 * total_force and total-moment are calculated
 */
}
transform_force_and_moment (phantom_pos, dev_pos,
                            total_force, total_moment,
                            phantom_force, dev_force);
apply_phantom_force (phantom_force);
apply_dev_force (dev_force);
}
get_phantom_pos ()
{
/*
 * this function determines the position of the 3 DOF haptic interface that the
 * tip of the tool handle is connected to
 *
 * it's form i& based on the geometry of the respective device
 */
}
get_dev_pos ()
{
/*
 * this function determines; the position of the subject invention in the world
 * frame
 *
 * the values b, 11, 12, 13, 14 are assumed to be known
 *
 */
    int            enc1;
    int            enc2;
    float          enc_angle_conversion_factor;
    float          d;
    float          a;
    float          c;
    float          theta_d;
    float          theta_a;
    float          theta_1;
    float          theta_2;
    float          theta_3;
    float          theta_4,
    three_vector   device_local_pos;
    three_vector   device_world_pos;
/*
 * enc1 and enc2 are the digital encoder values of the motors
 * they are multiplied by enc_angle_conversion_factor, which accounts for
 * the gear ratio between the inner links and the cable capstans PI/2. is also
 * added because they are both zeroed when their angles are at PI/2
 */
    enc1 = get_encoder_value (motor_1);
    enc2 = get_encoder_value (motor_2);
    theta_1 = PI/2. - enc_angle_conversion_factor * enc1;
    theta_2 = PI/2. - enc_angle_conversion_factor * enc2;
    d = 2. * b + 11 * cos (theta_1) - 12 * cos (theta_2);
    a =       11 * sin (theta_1) - 12 * sin (theta_2);
    c = sqrt (a * a + d * d);
    theta_a = atan2(a, d);
    theta_d = acos((13 * 13 + c * c - 14 * 14)/
              (2 * 13 * c));.
```

```
    theta_3 = PI - theta_d + theta_a;
    theta_4 = theta_d + theta_a;
    device_local_pos.x = (b + 11 * cos(theta_1) + 13 * cos(theta_3) +
            15 * cos(theta_4) + 16 * cos(theta_4 + PI/2.));;
    device_local_pos.y = (11 * sin(theta_4) + 13 * sin(theta_3) +
            15 * sin(theta_4) + 16 * sin(theta_4 + M_PI/2.))
    device_local_pos.z = 0.;
/*
 * device_local_pos is the device position in its own coordinate frame
 * we need to rotate and translate it back into the world frame
 */
    device_world_pos = transformation_matrix * device_local_pos;
    return device_world_pos;
}
transform_force_and_moment (phantom_pos, dev_pos,
                            total_force, total_moment,
                            phantom_force, dev_force)
{
/*
 * this function takes in the desired total_force and total_moment and
 * divides them between the two devices in the correct fashion so that
 * the user will feel the correct force and moment
 */
    three_vector stylus;
    three_vector stylus_hat;
    float         stylus_magnitude;
    three_vector moment_hat;
    float         moment_magnitude;
    three_vector dev_force_prime;
    three_vector dev_force_prime_hat;
    float         dev_force_prime_magnitude;
    float         temp;
    three_vector dev_force_world;
/*
 * stylus is the vector between the device_pos and phantom_pos
 */
    stylus            = dev_pos - phantom_pos;.
    stylus_magnitude  = stylus.magnitude();
    stylus_hat        = stylus/stylus_magnitude;
    moment_magnitude  = moment.magnitude ();
    moment_hat        = moment/moment_magnitude;
/*
 * dev_force_prime_minimum force vector required to achieve desired
 * moment
 */
    dev_force_prime         = ((moment_hat ^ stylus_hat) *
                               (mag_moment/radius_penta));
    dev_force_prime_magnitude = dev_force_prime.magnitude();
    dev_force_prime_hat     = dev_force_prime/
                               dev_force_prime_magnitude
    temp = -(((dev_normal * dev_force_prime_hat)/
             (dev_normal * stylus_hat)) *
             (dev_force_prime_magnitude));
/*
 * dev_force_world is the force vector that will be applied by the device
 * temp * stylus_hat is force_ganuna mentioned previously
 */
    dev_force_world = dev_force_prime + temp * stylus_hat;
    phantom_force = total_force - dev_force_world;
/*
 * dev_force is the device force in its own coordinate frame
 * we need to rotate dev_force_world into the devices local coordinate frame
 /*
    dev_force = transformation_matrix.inverse () * dev_force_world;
}
apply_phantom_force (phantom_force)
{
/*
 * this function converts the force vector phantom_force into
 * voltages to apply to the device's actuators.
 *
 * it's form is based on the respective device
 */
}
apply_dev_force(dev_force)
{
/*
 * this function converts the force vector dev_force into
 * voltages to apply to the device's actuators.
```

-continued

```
*/
two_vector tau;
two_vector actuator_voltages:
matrix jacobian;
float motor-constant;
jacobian = calc_jacobian ();
tau = jacobian.transpose() * dev_force;
/*
 * motor_constant takes into account both the gear ratio as mentioned in the
 * get_dev_pos() function and the scaling factor to convert from torque in
 * N*mm to volts that are the input of the motor
 */
actuator_voltages = tau * motor_constant;
apply_voltage's (actuator_voltages);
}
calc_jacobian()
{
/*
 * this function calculates the jacobian of the current configuration of the
 * device, based on the angles of all the joints calculated above in
 * get_dev_pos()
 */
double t1, t2, t3, t4, t5, t6, t7, t8, t9, t10, t11,
       t12, t13, t14, t15, t16, t17, t18, t19, t20, t23, t24, t26, t27,
       t30, t33, t34, t39, t42, t44, t45, t49, t51, t52, t57, t58, t59,
       t61, t62, t63, t65, t66, t68, t69, t74, t75, t81, t83, t85, t92;
       t95, t102, t103, t110, t115, t118, t121;
matrix jacobian;
t1 = sin(theta_1);
t2 = 11*t1;
t3 = 13*13;
t4 = sin(theta_2);
t5 = 12*t4;
t6 = t2-t5;
t7 = t6*t6;
t8 = cos(theta_1);
t9 = 11*t8;
t10 = cos(theta_2);
t11 = 12*t10;
t12 = 2.0*b+t9-t11;
t13 = t12*t12;
t14 = 14*14;
t15 = t3+t7+t13-t14;
t16 = 1/13;
t17 = t15*t16;
t18 = t7+t13;
t19 = sqrt(t18);
t20 = 1/t19;
t23 = atan2(t6,t12);
t24 = -.acos(t17*t20/2)+t23;
t26 = 13*sin(t24);
t27 = *t15*t15;
t30 = 1/t18;
t33 = sqrt(1.0-t27/t3*t30/4);
t34 = 1/t33;
t39 = 2.0*t6*11*t8-2.0*t12*11*t1;
t42 = t18*t18;
t44 = t19/t42;
t45 = t44*t39;
t49 = 1/t12;
t51 = 1/t13;
t52 = t6*t51
t57 = 1/(1.0+t7*t51);
t58 = (t9*t49+t52*t2)*t57;
t59 = t34*(t39*t16*t20/2-t17*t45/4)+t58;
t61 = t14+t7+t13-t3;
t62 = 1/14;
t63 = t61*t62
t65 = acos(t63*t20/2);
t66 = t65+t23;
t68 = 15*sin(t66);
t69 = t61*t61;
t74 = sqrt(1.0-t69/t14*t3.0/4);
t75 = 1/t74;
t81 = -t75*(t39*t62*t20/2-t63*t45/4)+t58;
t83 = t65+t23+0.5*0/3141592653589793E1;
t85 = 16 *sin(t83);
t92 = -2.0*t6*12*t10+2.0*t12*12*t4;
t95 = t44*t92;
```

-continued

```
t102 = (-t11*t49-t52*t5)*t57;
t103 = t34*(t92(t16*t20/2-t17*t95/4)+t102;
t110 = -t75*(t92*t62*t20/2-t63*t95/4)+t102;
t115 = 13*cos(t24);
t118 = 15*cos(t66)
t121 = 16*cos(t83)
jacobian (0,0) = -t2+t26*t59-t68*t81-t85*t81;
jacobian (0,1) = t26*t103-t68*t110-t85*t110;
jacobian (1,0) = t9-t115*t59+t118*t81+t121*t81;
jacobian (1,1) = -t115*t103+t118*t110+t121*t110;
return jacobian;
}
```

Having now described a few embodiments of the invention, and some modifications and variations thereto, it should be apparent to those skilled in the art that the foregoing is merely illustrative and not limiting, having been presented by the way of example only. Numerous modifications and other embodiments are within the scope of one of ordinary skill in the art and are contemplated as falling within the scope of the inventions limited only by the appended claims and equivalents thereto.

What is claimed is:

1. A system for providing realistic feedback to an individual utilizing a rigid haptic tool which manipulates an on-screen representation of said tool towards an on-screen object and over an on-screen obstacle, comprising:

haptic actuators for providing feedback forces on said tool responsive not only to the contacting of the tip of said on-screen representation of said tool with said on-screen object, but also those forces applied to a portion of said on-screen representation of said tool remote from said tip as a result of contact with said on-screen obstacle, wherein a set of said haptic actuators includes linkages that provide forces against a portion of the handle of said tool remote from the tip thereof in a plane at an angle to the longitudinal axis of said tool handle.

2. The system of claim 1, wherein said linkages includes a 5 bar linkage system and gimbaled ring coupled to said 5 bar linkage system and through which said tool handle passes.

3. The system of claim 2, wherein said 5 bar linkage system includes a base, a pair of sectors pivotally mounted on said base, and each having an extension therefrom corresponding to a bar in said linkage system, a pair of bars, each pivotally connected to the distal ends of said extensions and having their distal ends pivoted together and coupled to said gimbaled ring, said actuators including two sector drive actuators mounted to said base and acting their respective sectors to drive said sectors about the corresponding pivots thereof, thus to move said gimbaled ring to impart a force to said tool handle.

4. The system of claim 1, wherein the forces generated by said actuators are in accordance with physical characteristics assigned to said object and said obstacle.

5. The system of claim 4 and further including a computer and display for generating a virtual environment and wherein said on-screen representation of said tool, object and obstacle exist within said virtual environment with said physical characteristics assigned.

6. The system of claim 4, wherein said characteristics are selected from a group consisting of penetrability and contact resistance respectively for said object and said obstacle.

7. The system of claim 1, wherein said feedback forces are in accordance with:

$$\vec{F}_d = (\vec{M} \times \vec{S}) \frac{|\vec{M}|}{|\vec{S}|}$$

where $\vec{F}_d$ is the generalized force vector which will generate the moment, $\vec{M}$, where $\vec{M}$ is the moment to be applied to the tool handle about the tip of the tool to provide force feedback corresponding to the action of said on-screen tool, where $\vec{S}$ is the distance between the tip of said tool and the position on said tool handle where said force $\vec{F}_d$ is applied.

* * * * *